United States Patent

Woog et al.

[11] Patent Number: 5,934,908
[45] Date of Patent: Aug. 10, 1999

[54] HIGH-POWERED AUTOMATIC ELECTROMECHANICAL TOOTHBRUSH

[75] Inventors: Philippe-Guy Woog, Vesenaz/Geneva; Jean-Pierre Jousson, Geneva, both of Switzerland

[73] Assignee: L.P.A. Broxo S.A.-Les Produits Associes, Chene-Bourg, Switzerland

[21] Appl. No.: 08/890,472

[22] Filed: Jul. 9, 1997

[51] Int. Cl.⁶ ..................................................... A61C 15/00
[52] U.S. Cl. ......................... 433/216; 15/22.1; 15/167.1
[58] Field of Search .................................. 15/22.1, 167.1; 433/216, 118, 119

[56] References Cited

U.S. PATENT DOCUMENTS 5,378,153  1/1995  Giuliani et al. ......................... 433/216

Primary Examiner—Robert Warden
Assistant Examiner—Kaj K. Olsen
Attorney, Agent, or Firm—Kane, Dalsimer, Sullivan, Kurucz, Levy, Eisele and Richard, LLP

[57] ABSTRACT

A sonic toothbrush and method produces acoustic pressure. A predetermined bristle tip velocity is generated under applied load. A predetermined acoustic pressure is produced under applied load. A predetermined shear stress is produced and predetermined mechanical power is produced. Bacterial and microbial plaque under the gumline and in pockets is dislodged without physical contact between the plaque surface and bristle tips.

13 Claims, 1 Drawing Sheet

HIGH-POWERED AUTOMATIC ELECTROMECHANICAL TOOTHBRUSH

BACKGROUND OF THE INVENTION

The oral cavity is populated by a prodigious microbial flora that exhibits a unique successional colonization of enamel and subgingival root surfaces. A wide range of oral sites provide different ecologic conditions and are, therefore, populated by different commensal microbial combinations. The sequence of microbial colonization, regardless of location within the oral cavity, commences with the acquisition of salivary and/or crevicular fluid-derived pellicle.

As the process of successional microbial colonization of the gingival crevice and gingival margin proceeds uninterrupted, achieving critical mass between 5 and 10 days, gingivitis becomes evident at a clinical level. However, at a histologic level, gingivitis may be evident within 2 to 4 days of plaque accumulation. The inflammatory process sufficiently alters the ecological conditions so as to allow proliferation of supragingival plaque into subgingival areas. The subgingival plaque becomes progressively more Gram-negative and anaerobic in nature as the periodontal pocket deepens, leading ultimately to a chronic, progressive deterioration of the periodontium, referred to as adult periodontitis.

Brushing of the teeth is the most commonly used method for patient-facilitated removal of the dental microbial plaque. However, dental microbial plaque is frequently located in areas that prohibit its removal. This is particularly evident in such areas as the interproximal subgingival region. The bristles tips of an ordinary manual toothbrush and even automatic electromechanical toothbrushes cannot penetrate such areas, thereby allowing microbial plaque to accumulate, ultimately reaching critical mass, and inducing a host inflammatory response that leads to the common periodontal diseases (e.g., gingivitis and adult periodontitis).

Dr. Philipp G. Woog, one of the coinventors herein, invented the first automatic toothbrush and, after over 40 years of experience, firmly believes that a major cause of periodontal disease is absence of firmer and harder foods in modern day diets that would necessitate and require more deliberate and aggressive biting that would ensue in more exercise of the gums. Modern soft and refined foods require very little biting and other than firm fruit, modern foods including meats are generally soft. Dr. Woog believes certain groups of people with healthy gums such as the Yanomani Indians and Eskimos have healthy gums because raw vegetables and dry meat are common to their diets. These foods require biting that will inevitably result in pressure being applied to gums with attendant exercise and manipulation thereof because the gums under these circumstances will ride up on the upper teeth and down on the lower teeth.

Because conventional tooth brushing (manual and automatic) relies on direct contact between the brush bristle and the tooth surface to remove microbial plaque accumulations, those interproximal and subgingival areas that allow only limited or no access to bristle tips will generally exhibit undisturbed plaque formation. The sonic toothbrush was conceived in an attempt to overcome the problems presented by lack of access during manual toothbrushing—particularly the concept of cleaning beyond the bristles due to the acoustic effects generated at sonic frequencies being transmitted by the fluid environment that is associated with teeth during the act of toothbrushing.

Very recent and serious studies have shown that through the medium of a coupling fluid (saliva, toothpaste, etc.) the tips of the bristles of an electric toothbrush moving at a speed or a velocity of 1.5 m/s, create a reciprocating acoustic pressure and a shear stress, which effectively works to remove the dental plaque from the enamel surface at a distance of 2 mm beyond the bristle tips without bristle/tooth contact. This permits reaching very narrow spaces such as interdental spaces which even very thin bristles can hardly reach.

There are currently two known sonic automatic toothbrushes that have been commercialized under the names SONICARE and SENSONIC. The SONICARE device is purportedly marketed under U.S. Pat. No. 5,378,153 and the Sensonic device is allegedly quite similar. These devices claim to produce sonic vibrations, or low frequency acoustic energy, to enhance removal of bacterial plaque in vitro at distances beyond filaments. However, there appears to be little clinical data to support these in vitro findings.

The concept of sonic toothbrushes is based on the production of an acoustic effect being mediated through a liquid environment. However, patients do not brush their teeth by holding the brush tips 2 mm off of the tooth surface. Most users of the aforenoted sonic automatic toothbrushes place or force the brush tips against the tooth surfaces with various degrees of pressure. In fact, by placing the brush bristle against the tooth a severe dampening effect of sonic wave production occurs. This dampening effect could not only severely reduces the frequency of the sonic wave and therefore the acoustic effect, but also severely alters the phase of movement of the bristle tips, i.e., reducing the movement cycles per unit time of the bristle tip versus that at the bristle power source. In actual practice, the end result is a sonic tooth brush by design that has been converted to a highly efficient non sonic, mechanical brush in actual use. Any difference in clinical trials of the current sonic brushes versus mechanical and/or manual tooth brushes is likely a manifestation of the increased number of bristle cycles per unit time (more contact with the tooth surface) and not a result of acoustical effects.

It has been found that the torque and power level determines the effectiveness of cleaning and gum massaging with sonic automatic toothbrushes. An additional fundamental parameter, which should not be neglected is that an automatic toothbrush is not a simple "washing machine, but also and mainly a gum massaging instrument as well as a teeth brushing device by direct mechanical action (tooth enamel polishing, dislodging of wedged food particles, etc.).

To comply with these last requirements it is mandatory to introduce the notion of power under load, in other words, mechanical power at the level of the bristle tips under an applied force of about 350 g [3.5 N] against teeth and gums. It is under these conditions of load that the power must be sufficient to guarantee an acceptable amplitude of motion and frequency, and consequently velocity to offset any dampening of sonic energy.

It has also been determined that a practical technical solution to obtain an effective mechanical brushing power several times the one of existing electric toothbrushes and in order to assure sonic level of energy is to use a hydraulically powered toothbrush, as for example of the type disclosed in U.S. Pat. No. 4,561,251 and sold in the U.S. under the trademark "Woog Perio System" and "Periobrush" and supply it with boosted or increased parameter so that the bristle velocity, acoustic pressure and shear stress is constant and not dramatically reduced below critical values with applied forces increasing from 0 g to the relatively high value of 350 g. However, the Perio System toothbrush is somewhat inconvenient because it is bulky, heavy, and too big to carry. It is expensive and consumes high power while being complicated and of low reliability.

SUMMARY OF THE INVENTION

A principal object of the present invention is to provide an improved automatic oral hygiene sonic toothbrush operable at relatively high output torque and power for arresting periodontal disease and gum recession including plaque, gingivitis and periodontisis, and, in this regard, several orders of magnitude higher than commercially available electric toothbrushes including the aforenoted commercial sonic automatic toothbrushes.

Another object is to provide an improved sonic automatic toothbrush of the foregoing type capable of generating a high number of brushing cycles per unit time that will agitate a liquid environment overlying microbial plaque to such an extent as to result in removal of microbes without physical contact between the plaque surface and the bristle tips.

A further object is to provide an improved sonic automatic toothbrush of the foregoing type that produces the necessary acoustic pressure to dislodge significant amounts of bacterial plaque even under the gumline and in pockets including interproximal and subgingival areas while maximizing the shine and whiteness of the teeth and, at the same time, stimulating the gums to prevent and arrest periodontal disease.

A still further object is to provide an improved sonic automatic toothbrush of the foregoing type that possesses an ultra speed arcuate sweeping and sonic action, that eliminates plaque; massages gums, leaving them firmer, pinker and healthier; effectively polishes and whitens teeth; and dislodges plaque even below the gumline and in pockets including interproximal and subgingival areas.

An important object is to provide an improved sonic automatic toothbrush of the foregoing type in which the bristles movement mimics the act of biting into firm and hard foods and with enough torque under loads to restore and maintain good gingival health.

The scientific studies conducted in recent years, establish precisely what the brushing parameters of a sonic electro-mechanical or automatic toothbrush should be in order to obtain maximum efficiency. These various studies have enabled the following parameters to be set:

a) The maximum speed of the bristle tips under applied loads must be at least 1.5 m/s. This speed depends on the frequency of oscillation or reciprocating rotation of the brush stem which must have specific minimum values and on the amplitude of the motion of the brush stem bristle tips.

b) Since in most cases the brush's bristles, even if they have a small diameter, cannot penetrate into the interdental spaces or the sub-gingival pockets, it is essential, using the "coupling" liquid available, namely toothpaste, saliva and, if applicable, water, to produce beyond the bristle tips, an acoustic pressure and a shear stress capable of removing a significant amount of bacterial plaque at a distance of at least 2 mm.

c) At 2 mm from the bristle tips, the acoustic pressure under applied loads should have a value of over 1.5 KPa and the shearing stress under applied loads should be over 50 Pa.

d) Power output (mechanical) under applied loads should be 2.5 to 6 W.

These in-depth studies and measurements have made it possible, for the first time, to accurately quantify the various aforenoted parameters, under conditions which are very close to those of practical use.

With respect to the present invention, it has also been found that the device of this invention removes dental plaque effectively at a distance of 2 mm from the bristle tips (without any contact between the bristles and the tooth), which means that inaccessible places such as the interdental spaces, gingival pockets, etc. can be cleaned, by virtue of the remote transmission of the undulatory energy of the motion of the device's bristle tips via a coupling liquid such as toothpaste or saliva. Under conditions very close to those of practical use, remote transmission of energy was obtained by virtue of toothpaste froth as a coupling means.

Finally, a comparison of recommended values for the 4 parameters—bristle tip velocity, acoustic pressure, shear stress and power—with those obtained with the brush of the present invention, reveals that the latter values are far higher than the recommended values and higher than the aforenoted commercially available sonic toothbrushes.

Bristle tip velocity will govern rate of oscillation, angle of oscillation, increased bristle length and torque.

As several factors play a role in actual practice (e.g., coefficient of friction) it is preferred to use the force (applied load) as another one of the most important parameters, of application of the applicator against the surface to be treated.

For purposes of this disclosure, certain definitions should be understood, as set forth below:

a) Sonic effect(s) Means that sonic waves are produced in the coupling fluid or froth and transmit energy capable to have a remote action.

b) Acoustic effect(s) This produces a certain level of alternative acoustic pressure in the coupling fluid to produce a remote action.

c) Cleaning beyond the bristles Means remote cleaning/massaging action without any contact with the applicator tip (typical value at 2 to 4 mm beyond the tip of the applicator).

d) Acoustic pressure Means alternating pressure field in the coupling fluid produced by the applicator tip movement.

e) Sonic frequency In general, it is the range of audio frequency, normally from 20 Hz to 20,000 Hz [not to be confused with ultrasonic range starting at 20,000 Hz to 2 MHz (Mega Hz)].

f) Shear stress The alternating shear stress beyond the applicator tip create in the coupling fluid "scrubs" the surface to be cleaned without physical contact of the applicator tip.

g) Bristle tip velocity Means the maximum velocity of displacement of the tip of an applicator (for instance with a sinusoidal motion Vmax=A 2 $\pi$f) which produces a combined scrubbing action (with mechanical contact) and a beyond the applicator tip cleaning/massaging action.

DETAILED DESCRIPTION

Figure 1:
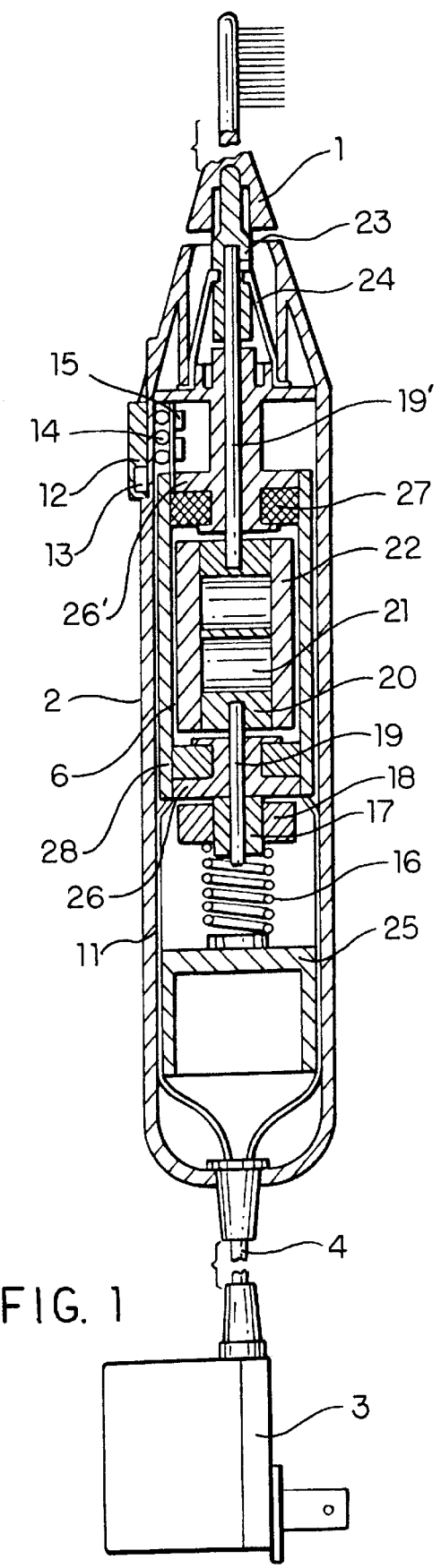
FIG. 1 is a longitudinal sectional view of a sonic electric toothbrush incorporating the teachings of this invention.

FIG. 1 shows the motor body 2 which will be described in detail later on and which drives the brush head 1 in an oscillating motion. This electric motor 6 is powered by an extra safety low voltage, either directly from the main through a step down converter 3 [AC/AC safety transformer] and a cord set 4 or (see FIG. 2) by two rechargeable batteries (e.g. NiCd) 5 and a square wave oscillator 7.

In this last form of execution the rechargeable batteries 5 are loaded by an inductive charging unit 8 where the primary coil 9 induces magnetic energy into a secondary coil 10 located in the casing 11 of the device when it is placed in the lodging 12 of the inductive charging unit 8.

FIG. 1 shows in detail the switch control knob 12 located outside of the casing 11 of the device, this control knob 12 comprising a permanent magnet 13 which allows to control reed switches 14 located inside of the casing 11 which together with a system of resistors 15 allows to switch OFF and to switch ON the motor on three energy levels [Low—Medium—High] which allows the use of the device according to a well defined posology.

The brush head 1 is driven by the movable part of the oscillating motor 6 which is mainly composed of a recall helical spring 16, a fixation sleeve 17, an inertial mass 18 allowing to tune the resonance frequency to the frequency of the power supply, this in order to obtain an optimal brushing energy, a shaft 19-19' in two half parts, a rotor hub 20, two high energy permanent magnets 21 such as NdFeB or SaCo, two magnetic "poles" 22 in soft iron, a brush holder 23 which holds and drives the brush head 1.

A resilient sealing mean 24 guarantees the watertightness between the brush holder 23 and the casing 11. It is evident that one end of the recall helical spring 16 is fixed to the not movable part 25 bounds up with the casing 11.

Figure 2:
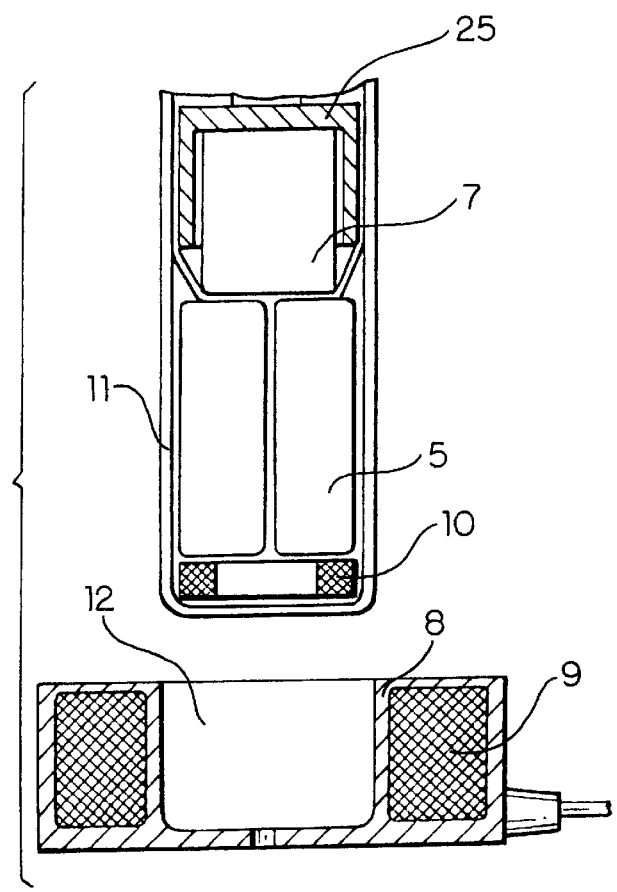
FIG. 2 is fragmentary view showing a portable rechargeable battery driven sonic toothbrush of this invention.

The static part of the motor 6 is composed of two bearings 26 and 26', two energizing coils 27 electrically connected to the power supply described in FIG. 1 and 2 and this through the reed switches 14 and the system of resistors 15, a stator 28 in soft iron, made in one or, two parts, which surrounds the energizing coils 27. This stator 28 is also used to hold the two bearings 26, 26', the whole being accurately located in the casing 11.

The recall helical spring 16 as well as the resilient sealing mean 24 (having a very low effect) insure the return to the still position 0 of the brush head 1.

When the energizing coils are powered the created magnetic field drives the rotor and also the brush head 1, this in both directions from the still position 0, and with synchronous frequency of the power supply.

Figure 3:
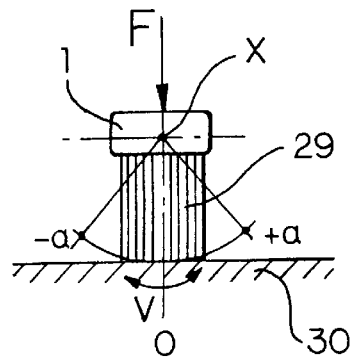
FIG. 3 is a diagrammatic view showing the imposed oscillator motion by the oscillating motor which produces oscillating motion of the brush head.

FIG. 3 shows the imposed motion by the oscillating motor on its shaft X which produces an arcuate oscillating motion at the brush head 1 level. The bristle tips 29 of the brush head 1 which are loaded by an application force F, describes against the surface 30 of the teeth or gums, and arcuated oscillating motion having an amplitude A from O to −a and from O to +a. The velocity V of the bristle tips and its desired effects is well defined herein.

With specific reference to FIG. 3, as a result of the oscillating motion of the bristles through a prescribed arc, pressure in the fluid surrounding the teeth builds up, especially in the region where the gum meets the teeth and the periodontal pocket. The sweeping back and forth movement of the bristles, causes the liquid to flow back and forth at velocities approaching that of the brush. The pressure beyond the tips of the bristles through the medium of the coupling liquid is exerted on the interdental and subgingival region. The dental liquid will normally be saliva, with additional water and toothpaste. Any dentifrice or bacteriocidal solution may also be used or substituted.

According to the present invention, the bristles also provide a significant scrubbing action without detracting from or jeopardizing the desired sonic action and acoustic pressure even when there is desired firm/strong contact between the bristles and teeth. This scrubbing action removes plaque mechanically particularly in those regions where the bristles physically contact the plaque.

More importantly, as the scrubbing action takes place, the movement of the bristles creates an alternating pressure field about the teeth while maintaining a bolus of liquid near the bristle tips. When the moving bristles are positioned over the interdental regions, the pressure field created in the liquid by the action of the bristles, extends into those regions which are not reached by the bristles themselves. The pressure field also acts to clean bacteria from the periodontal pockets.

The scrubbing action coupled with the sonic effect generates a shear force which is then in turn applied to bacteria on the teeth. The action of the bristles forces the fluid to flow at a particular velocity approaching the velocity of the bristle tips across the surface of the teeth. In this manner, the required shear stress is produced to dislodge the bacteria on the surface of the teeth contacted by the bristles tips and spaced therefrom including the interdental channel between adjacent teeth.

The scrubbing action and effects of the acoustic pressure is enhanced by the abrasion created by the toothpaste or dentifrice employed which induces an erosion of the plaque aided by the turbulent flow of the liquid bolus.

The present invention contemplates the rotary oscillating motion through a preset arc of the aforenoted preferred practical embodiment as well as the back and forth or pendulum movement of the embodiments of U.S. Pat. No. 5,378,153 and a reciprating axial movement or any other periodic back and forth reciprocal or oscillating movement provided the parameters of bristle tip velocity, acoustic pressure and shear stress of this invention are maintained.

As a result of the advanced technology of the high speed arcuate action of the bristles and high generated torque, dental plaque is removed even beyond the tips of the bristles even with the bristles impinging or contacting the teeth and gums within one minute compared to seven minutes of manual brushing and within this time frame providing adequate gum massage compared to 30 minutes of gum massaging by hand.

Thus, in the case of toothbrushing, the device of this invention assures by means of a coupling fluid, a remote action, that means without any contact with the working instrument, optimum values of acoustic pressure and shear stress measured at 2 and 4 mm from the tip of the instrument. This remote action is maintained even when forces are applied against the working toothbrush. The desired values of acoustic pressure and shear stress are maintained as a function of the applied force which can reach the very high value of 350 g. [3.5 N]

The maximum velocity of displacement of the working tip of the instruments is a basic factor and should not be by any means smaller than certain values in terms of the function of the applied force and also based on the function of the described motion, whether reciprocating, continuous or vibrating. For instance, for a sinusoidal oscillating motion, the maximum velocity is defined by $Vmax = A\, 2\, \pi f$ where "A" is the amplitude and "f" the frequency of the motion. As stated, the maximum speed of the bristle tips must be at least 1.5 m/s.

In order to adapt to the user's wishes, the device of this invention is equipped with an energy adjustment system. The instruments or accessories are built for the function for which they are foreseen and even if they are soft and/or flexible, they guarantee the defined values for the various parameters such as acoustic pressure, shear stress, max. velocity, etc. The device of this invention is designed to be able to produce a mechanical power capable to respect and achieve these various parameters described.

The device of this invention may be advantageously powered by means of a variable source of energy or one limited in time, such as batteries, accumulators, etc. It must be capable to respect the imposed requirements mentioned above and without interference (such as loading, etc.) during 5 cycles of 3 min. running time followed by 1 min. of resting time (off period) and this under the maximum power and/or load condition.

According to the various uses, i.e., dental cares and gum massaging, the device of the invention does not experience any excessive temperature rise, is silent (not noisy at least) and furthermore is easy to handle with only one hand because of its small dimensions (max. diameter 45 mm/max length 200 mm) as well as its light weight (max. 400 g.). Accordingly, the device is portable for travel purposes and the like.

The following parameters characterize the new appliance disclosed herein:

Its dimensions, weight, simplicity, safety and ergonomics must enable it to be used by the general public, and children in particular. When it is deemed to be portable, it should preferably not have any cord hampering its mobility and be equipped with a rechargeable battery.

It must be equipped with interchangeable and personal toothbrushes, the dimensions and rigidity of which match the appliance itself, but above all match the practical requirements for use and in particular its performance as a motion transmission element and its performance vis-a-vis the teeth and gums, without overlooking the fact that the brush must not allow bacterial proliferation.

It must drive the active part of the brush in an alternating movement, whether this is axial, arc-shaped (physiological), rotary or other.

The frequency of this movement or rate of oscillation must be between 40 and 500 Hz, but preferably between 50 and 250 Hz.

The angle of oscillation should be between 20 to 80°, depending on frequency.

The length of bristles should be increased to 10 to 20 mm.

The amplitude must be between 0.5 and 10 mm, but preferably between 2 and 6 mm. Amplitude A is the maximum value of the sinusoid in relation to position O of an alternating movement. As a result, the "peak-to-peak" value is 2A and the full travel covered in one cycle is 4A.

These frequency and amplitude values enable one of the very important parameters to be defined, viz. the maximum speed of movement of the ends of the bristles comprising the brush:

$$V_{PEAK} \text{Minimum} = 1.5 \text{ m/s}$$

The combination of the rate and angle of oscillation together with the length of bristles must be such as to assure a minimum velocity of the bristle tip equal to or greater than 1.5 m/s.

Torque should be 300 to 600 cmg (calculated and depending on the coefficient of friction on the surface.

Furthermore, it must have a significant mechanical power in order to guarantee its brushing and massaging effectiveness, not when working off-load, measuring the power available on the drive shaft, which is the normal practice, but by measuring it in operation, under a load consisting of high application forces.

In concrete terms, an application force of 3.5 N (approximately 350 g) is essential to make a normal toothbrush, i.e. one with bristles of a diameter of 0.14–0.17 mm, penetrate as far as possible inside the interdental spaces; these zones are critical as they are difficult to gain access to. Under these loading conditions, an average minimum integrated mechanical power of 2.5 W must be developed by the active part of the brush in order to guarantee brushing and massaging. This average value enables a peak value to be calculated.

Obviously, the power supply, the motor, the elements transmitting the movement to the teeth and gums must be designed with appropriate dimensions.

Finally, it must also be possible to use the appliance under low application forces; in the case, as the power consumed is close to O, the frequency and amplitude values required and defined under an application force of 3.5 N (approx. 350 g) must not vary by more than ±50% and preferably ±30%, with a view to preventing discomfort or even traumatisms. This constancy of the brushing parameters is obtained either through the principle of the appliance, or using a built-in device, or because the power is great enough for the load applied to have little or no influence.

In all cases, it is preferable for the appliance to be equipped with a power regulator, which enables care posology to be monitored.

We claim:

1. A high torque and high power sonic automatic oral toothbrush for cleaning teeth and massaging gums and being designed and so constructed and arranged to produce acoustic pressures to dislodge bacterial and microbial plaque under the gumline and in pockets without physical contact between the plaque surface and the bristle tips while maximizing the shine and whiteness of the teeth, and, at the same time, stimulating the gums to prevent and arrest periodontal disease, a body member which includes a shaft mounted for oscillating motion, a set of bristles having free end tips, the set of bristles being located close to one end of the shaft; and means in the body member for moving the shaft and hence the set of bristles such that the amplitude of the bristle tips do not vary by more than ±30% when an applied load on the bristle tips increases from 0 to 350 g (3.5 N), such amplitude being sufficient to produce a remote sonic cleansing and massaging action with a coupling fluid at a location at least 2 mm beyond the bristle tips.

2. The invention according to claim 1 wherein the mechanical power is a value between 2.5 and 6 W.

3. The invention according to claim 1 wherein the tip velocity is a value of at least 1.5 m/5.

4. The invention according to claim 1 wherein the acoustic pressure is a value of at least 1.5 kPa.

5. The invention according to claim 1 wherein the shear stress is a value between 50 Pa and 500 Pa.

6. The invention according to claim 1 wherein the toothbrush has means for producing a high number of brushing cycles per unit time and thereby an ultra speed arcuate sweeping and sonic action of a coupling liquid bolus to produce acoustic pressure and shear stress capability for removing plaque at a distance of at least 2 mm.

7. The invention according to claim 1 wherein at 2 mm from the bristle tips, the acoustic pressure has a value of at least 1.5 KPa and shear stress has a value of 50 Pa.

8. The invention according to claim 1 wherein the applied load is 350 g without diminishing the sonic action and acoustic pressure at a distance between the tips of the bristles of 2 mm from the teeth.

9. The invention according to claim 1 wherein at applied loads from 0 to 350 g the bristle tip velocity, acoustic pressure and shear stress remain substantially constant.

10. The invention according to claim 1 wherein the bristle tip velocity is at least 1.5 m/s, the acoustic pressure is at least 1.5 KPa and the shear stress is at least 50 Pa.

11. The invention according to claim 1 wherein the movement at the active brush head level is an arcuate oscillating motion with an angle of brushing between 20 and 80 degrees.

12. The invention according to claim 1 wherein the natural oscillating frequency of the moving part is tuned whereby the amplitude of the bristle tips will remain constant or increase in response to the applied load (0 to 350 g).

13. A method of producing acoustic pressures to dislodge bacterial and microbial plaque under the gumline and in pockets without physical contact between the plaque surface and the bristle tips while maximizing the shine and whiteness of the teeth, and, at the same time, stimulating the gums to prevent and arrest periodontal disease, oscillating a shaft mounted on a body member, said shaft including a set of bristles having free end tips, the set of bristles being located close to one end of the shaft; moving the shaft and hence the set of bristles such that the amplitude of the bristle tips does not vary by more then ±30% when an applied load on the bristle tips increases from 0 to 350 g (3.5 N), such amplitude being sufficient to produce a remote sonic cleansing and massaging action with a coupling fluid at a location at least 2 mm, beyond the bristle tips.

\* \* \* \* \*